United States Patent
Themelis

(10) Patent No.: US 11,196,942 B2
(45) Date of Patent: Dec. 7, 2021

(54) IMAGE PROCESSING DEVICE AND METHOD, AND MEDICAL OBSERVATION DEVICE COMPRISING SUCH AN IMAGE PROCESSING DEVICE, USING AN INTENSITY OR BRIGHTNESS-DEPENDENT VARIATION OF A PSEUDOCOLOR PATTERN CHARACTERISTIC

(71) Applicant: Leica Instruments (Singapore) Pte. Ltd., Singapore (SG)

(72) Inventor: George Themelis, Lindau (DE)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 0 days.

(21) Appl. No.: 16/739,189

(22) Filed: Jan. 10, 2020

(65) Prior Publication Data
US 2020/0252554 A1    Aug. 6, 2020

(30) Foreign Application Priority Data

Jan. 31, 2019  (EP) ..................................... 19154875

(51) Int. Cl.
| | |
|---|---|
| *A61B 1/045* | (2006.01) |
| *H04N 5/262* | (2006.01) |
| *A61B 90/20* | (2016.01) |
| *A61B 1/00* | (2006.01) |
| *A61B 1/06* | (2006.01) |

(52) U.S. Cl.
CPC ....... *H04N 5/2621* (2013.01); *A61B 1/00009* (2013.01); *A61B 1/00045* (2013.01); *A61B 1/0638* (2013.01); *A61B 90/20* (2016.02)

(58) Field of Classification Search
None
See application file for complete search history.

(56) References Cited

U.S. PATENT DOCUMENTS

| | | | | |
|---|---|---|---|---|
| 7,796,801 | B2 * | 9/2010 | Kitamura | ................. G06K 9/48 |
| | | | | 382/141 |
| 2015/0276602 | A1 * | 10/2015 | Ishihara | ............... A61B 1/0638 |
| | | | | 250/458.1 |

FOREIGN PATENT DOCUMENTS

| | | |
|---|---|---|
| EP | 3205254 A1 | 8/2017 |
| EP | 3248531 A1 | 11/2017 |
| EP | 3410394 A1 | 12/2018 |

\* cited by examiner

*Primary Examiner* — Christopher G Findley
(74) *Attorney, Agent, or Firm* — Hodgson Russ LLP

(57) ABSTRACT

An image processing device (100) for a medical observation device (102), such as a microscope (104) or endoscope, is disclosed. The image processing device (100) comprises an image processor (106). The image processor (106) is configured to obtain a digital pseudocolor pattern (116), which has a pattern characteristic (118) and comprises a pseudocolor (120). The image processor (106) is further adapted to combine the digital pseudocolor pattern (116) with an input area (122) of retrieved digital input image (108, 110), thus forming a patterned region (124). Moreover, the image processor (106) is adapted to vary the pattern characteristic at a location (126) in the patterned region (124) depending on one of the intensity (I) and brightness (B) at a corresponding location (128) in the input area (122) of at least one of the digital input images (108, 110) and retrieved digital input image (108, 110); and to output at least one digital output image (130) comprising the patterned region (124).

15 Claims, 8 Drawing Sheets

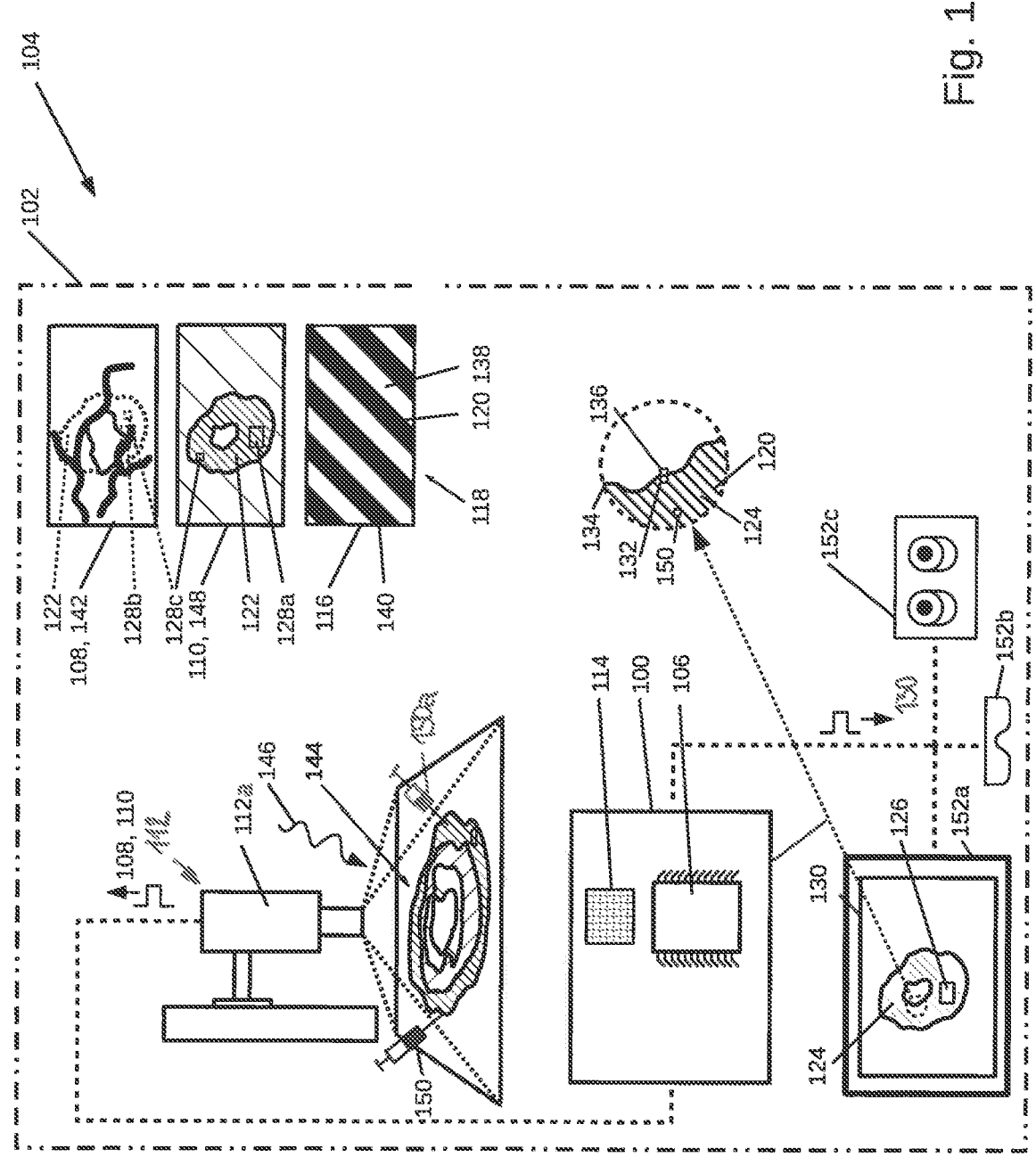

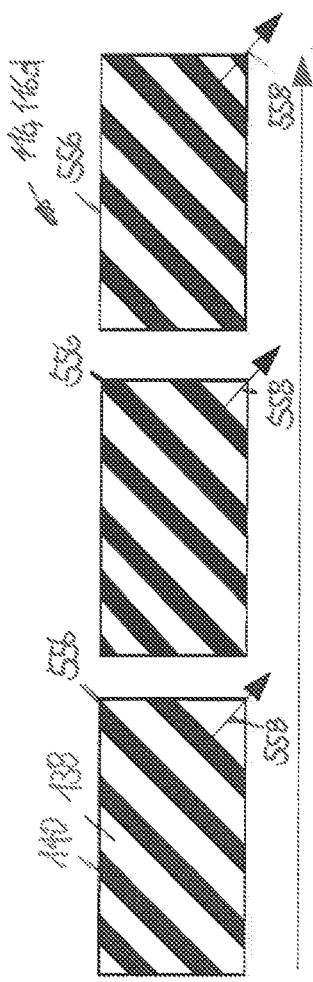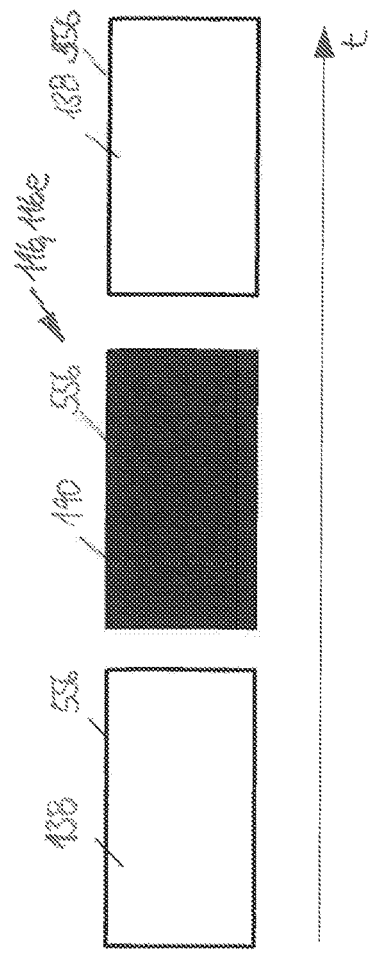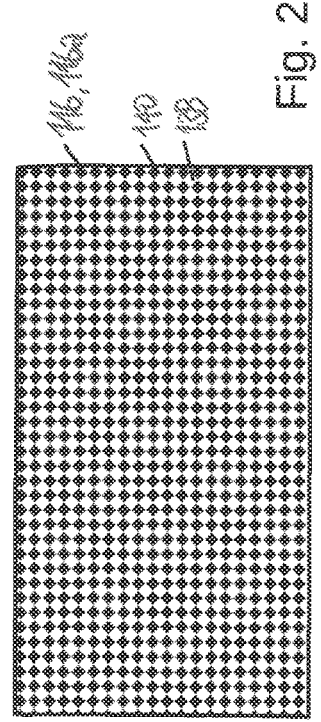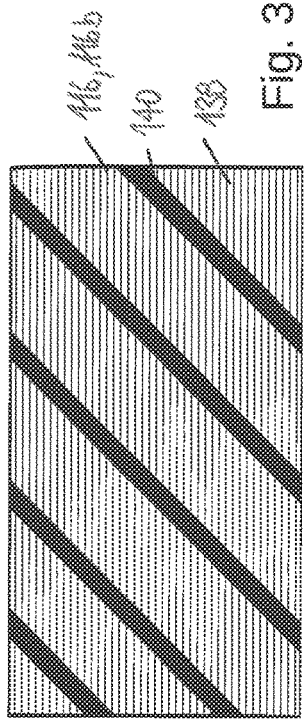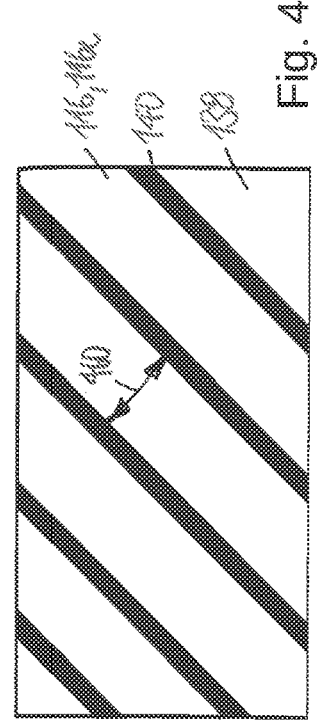
Fig. 5
Fig. 6
Fig. 2
Fig. 3
Fig. 4

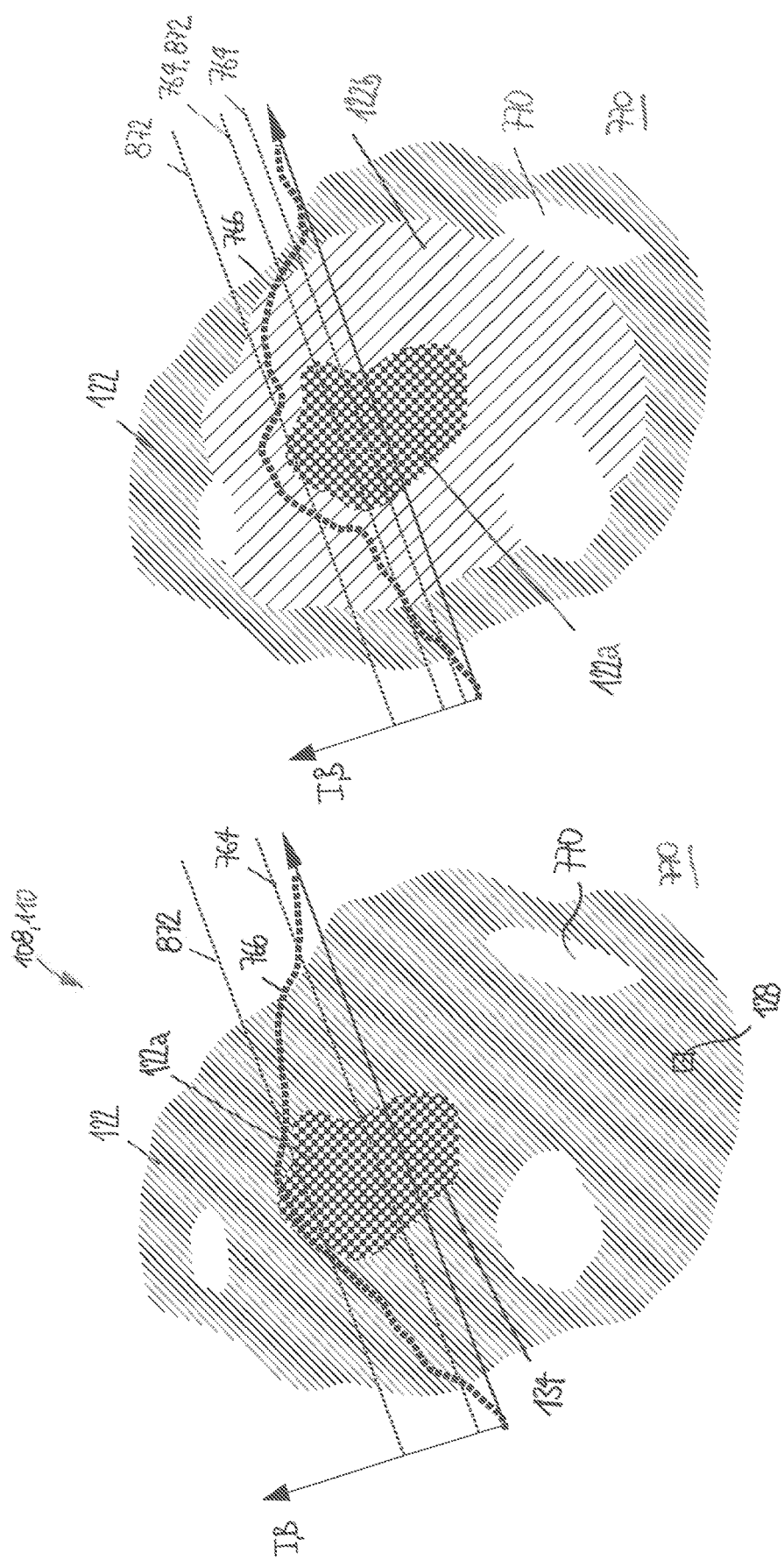

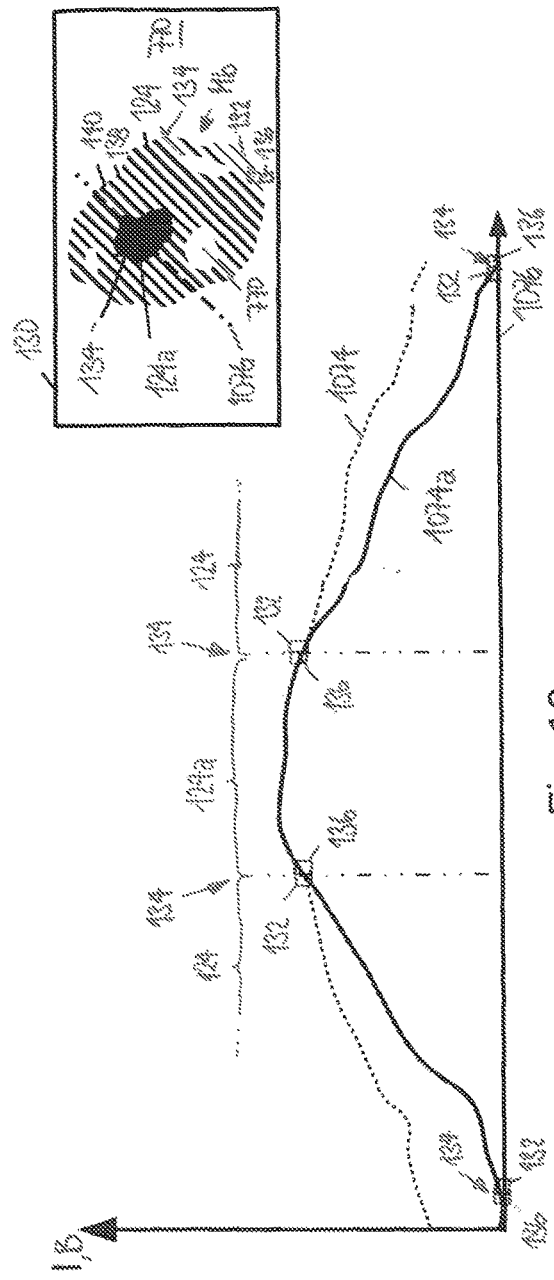

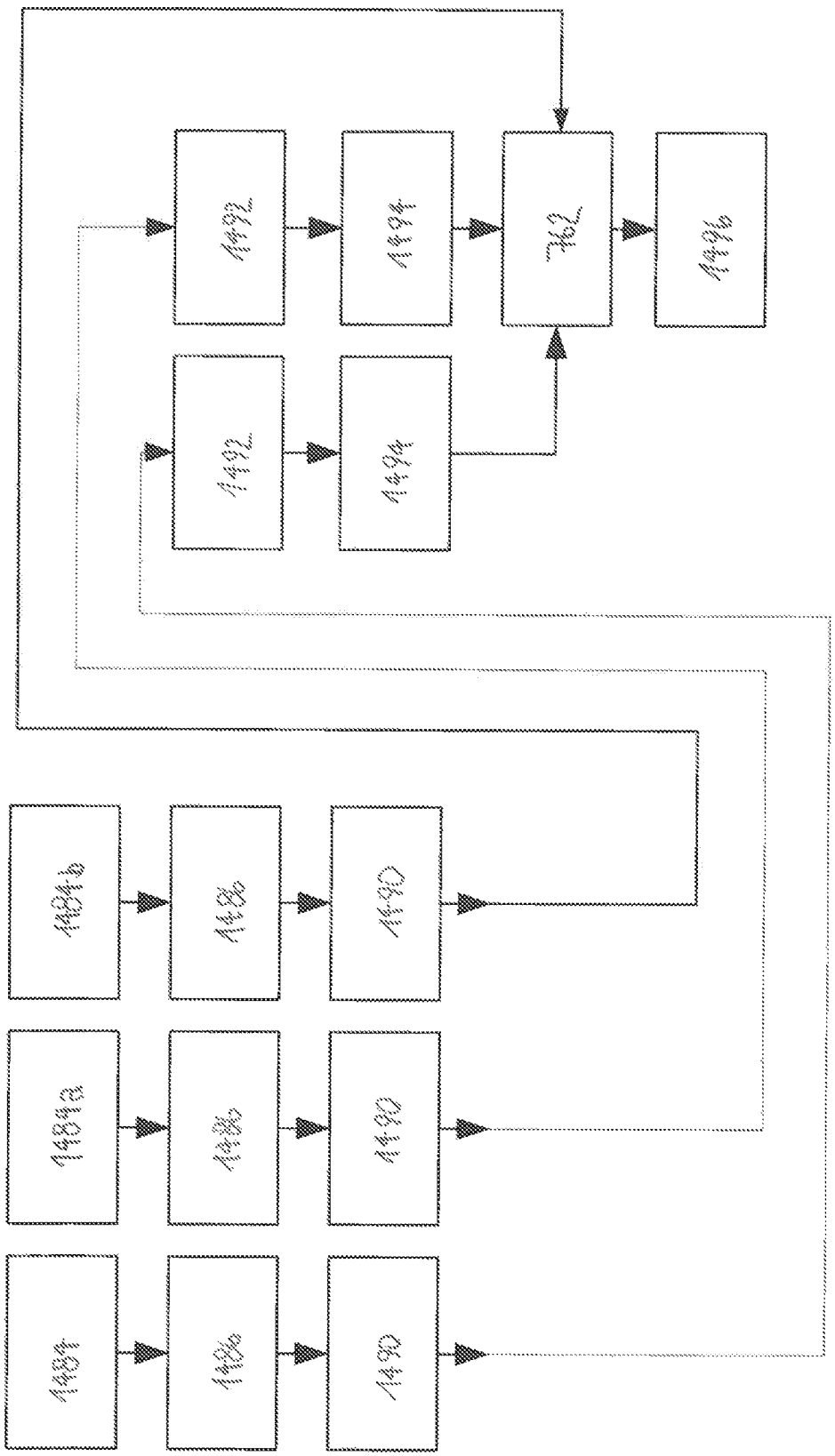

IMAGE PROCESSING DEVICE AND METHOD, AND MEDICAL OBSERVATION DEVICE COMPRISING SUCH AN IMAGE PROCESSING DEVICE, USING AN INTENSITY OR BRIGHTNESS-DEPENDENT VARIATION OF A PSEUDOCOLOR PATTERN CHARACTERISTIC

CROSS REFERENCE TO RELATED APPLICATIONS

This application claims priority of European patent application number 19154875.9 filed Jan. 31, 2019, the entire disclosure of which is incorporated by reference herein.

TECHNICAL FIELD

The invention relates to an image processing device for a medical observation device, such as a microscope or endoscope, to a medical observation device comprising such an image processing device, and to an image processing method, for example, a microscopy or endoscopy method.

BACKGROUND

There is currently a need for medical observation devices, such as microscopes or endoscopes, or for image processing devices that are used in conjunction with such a medical observation device, to be capable of automatically determining regions of interest. A region of interest may, for example, be a part of an observed tissue or an observed cell, which can be discerned by its optical characteristics, such as reflectance or fluorescence, and which needs to be identified for carrying out a further processing step. The region of interest may for example be a structure, such as a blood vessel or a tumor. In case of a tumor, the further processing step may be a biopsy or an excision.

Often, however, there is an ambiguity of whether an observed area is indeed a region of interest or whether it belongs to the background, which is currently not of interest. This may particularly be the case if a region does not satisfy all the criteria that are used to unambiguously define the region of interest. For example, the fluorescence intensity in an area may be just below a threshold which would clearly mark it as a tumor. In another example, the intensity or brightness color of an area may be just below a threshold which would clearly mark it as a blood vessel.

Therefore, according to one aspect of the invention, an image processing device, a medical observation device, and an image processing method are provided for identifying and/or displaying such ambiguous regions of interest.

SUMMARY

The above need is addressed by an image processing device which comprises an image processor, wherein the image processor is configured to obtain a digital pseudocolor pattern, the digital pseudocolor pattern having a pattern characteristic and comprising a regularly varying pseudocolor, to combine the digital pseudocolor pattern with an input area of a retrieved digital input image, thus forming a patterned region, to vary the pattern characteristic and the location in the patterned region depending on one of the intensity and brightness at a corresponding location in the input area of at least one of the digital input images and a further retrieved digital input image, and to output at least one digital output image comprising the patterned region.

The above need is further addressed by a medical observation method which comprises such an image processing device, a camera system configured to record one or more digital input images, and at least one display device configured to display the at least one digital output image. A preferred embodiment of the medical observation device is a microscope, such as a laboratory microscope, which may be used for investigating cell structures, a surgical microscope for performing surgery, in particular on the human body, e.g. neurosurgery or eye surgery, or an endoscope, in particular a surgical endoscope.

Finally, the above need is addressed by an image processing method, which comprises the steps of retrieving one or more digital input images; generating at least one digital output image from the one or more digital input images; and outputting the at least one digital image for at least one of displaying and further processing; wherein the step of generating the at least one digital output image from the digital input image comprises the steps of; combining a digital pseudocolor with at least one input area of at least one of the one or more digital input images to create a patterned region, wherein the digital pseudocolor pattern has a pattern characteristic; and adjusting the pattern characteristic at a location of the patterned region depending on one of an intensity and brightness at a corresponding location in the input area of at least one of the one or more digital input images.

The above method and devices allow to quickly differentiate between ambiguous and unambiguous regions of interest. When displaying an ambiguous region of interest, which does not satisfy all criteria currently set for a region of interest, care must be taken to mark them differently from an area which meets all the criteria for a region of interest. If an ambiguous region of interest and an unambiguous region of interest would be marked in the same manner, the user may not be able to recognize the difference and draw wrong conclusions about further steps. If, for example, the medical observation device is a surgical microscope or endoscope, a surgeon may wrongly decide that an ambiguous region of interest is a tumor which needs to be excised. If the ambiguous region of interest is in fact not a tumor, but an artifact, removal of the erroneously-marked tumor may pose a serious risk to the patient. Further, if all dubious regions of interest need to be confirmed manually, e.g. by varying the criteria for displaying the region of interest, the surgery will become more time-consuming and exhausting for the surgeon.

By varying the pattern characteristic at a location in the patterned region depending on one of the intensity and brightness at a corresponding location of the input area, the digital pseudocolor pattern is not uniformly applied, but changed according to the content of the area where it is applied. This allows ambiguous regions of interest to be displayed differently from unambiguous regions of interest.

For example, if a region of interest is based on the fluorescence of a fluorophore which is collected in the region of interest, the intensity of the fluorescence in the input area may be decisive on whether an area is classified as a region of interest or not. Varying the pseudocolor pattern on intensity or brightness allows a user to immediately recognize a region of interest, which may not clearly be a tumor.

Another example is e.g. a blood vessel, which may be identified by its color. Blood vessels, where the intensity in a specific color range is not sufficiently high enough to be unambiguously qualified as a blood vessel, can thus be marked with a different pseudocolor pattern characteristic.

The above image processing device, medical observation device and method thus greatly improve handling of the medical observation device by positively interacting with the user using technical effects.

The above image processing device, medical observation device and method may be further improved by comprising one or more of the additional features which are described in the following. As it is explained below, each of these additional features has its own technical effect and may be independently combined with any one of the other additional features. The additional features may be indiscriminately applied to the image processing device, the medical observation device and/or the image processing method. It is to be understood, that whenever a process step is explained in the following without explicitly mentioning the image processing system, the image processing device may be correspondingly configured to carry out this processing step. Vice versa, if it is stated that the image processor is configured to carry out a process step, this process step may also be part of an embodiment of the image processing method comprising or requiring the image processing device.

For example, the image processor may be configured in one embodiment to obtain the one or more digital input images by retrieving them from at least one of a camera system and a memory device. The camera system may comprise a CMOS or a CCD camera. The camera system may, alternatively or cumulatively, comprise an RGB camera, a multispectral camera and/or a hyperspectral camera. The camera system may further comprise a camera which is configured to record one or more digital input images in one or more wavelength bands comprising white light, IR, NIR and/or UV light. The memory device may comprise a hard disk drive, a memory card, a memory stick, a memory bank, and/or at least one of magnetic and optical disks. The memory device may further comprise volatile and/or volatile memory.

The location, at which one of the intensity and brightness in the input area is determined, may be a single pixel in one of the one or more digital output images. The location may also be a set of preferably contiguous pixels in one or more digital input images. A location in the input area may be considered to correspond to the location in the patterned region if it has at least one of the same geometrical position within the at least one digital input image and the at least one digital output image as derived from the at least one digital input image, and/or the same geometrical position within the same image feature as extracted by a pattern recognition algorithm from the one or more digital input images. The input area may be a feature in the one or more digital input images that has been extracted, in particular by the image processing device, using a pattern recognition algorithm. Matching locations in the patterned region and in the input area improves the accuracy of the rendition in the one or more digital output images and makes sure that the pseudocolor pattern faithfully renders what is observed in the input area.

In one embodiment, obtaining a digital pseudocolor pattern may comprise at least one of retrieving the digital pseudocolor pattern, e.g. from a memory device, and generating the digital pseudocolor pattern, e.g. using a function stored in the image processing device. The image processor may, for example, comprise a memory, in which pre-defined digital pseudocolor patterns or pre-defined functions for generating one or more digital pseudocolor patterns are stored.

The digital pseudocolor pattern may, in another embodiment, comprise a pseudocolor which may be stored in a memory device or which may be generated using a function. The function may be stored in the image processing device. For example, the image processor may be configured to determine a pseudocolor of the digital pseudocolor pattern automatically from a set of stored pseudocolors. The pseudocolor preferably is a color which is not comprised in any of the one or more digital input images on which the one or more digital output images are based.

The pattern characteristic distinguishes one digital pseudocolor pattern from another. The pattern characteristic may comprise at least one of a pseudocolor, intensity, brightness, transparency, contrast, geometric shape, temporal rate of change, and spatial rate of change of the digital pseudocolor pattern. Any of these pattern characteristics may be varied at a location depending on one of the intensity and brightness at the corresponding location in the input area.

The digital pseudocolor pattern may be at least one of a temporally and spatially varying digital pseudocolor pattern. A temporally varying digital pseudocolor pattern has a temporal regularity, e.g. a dominant temporal frequency or, equivalently, rate of change, which governs the regular changes or repetitions of the digital pseudocolor pattern over time. One example of such a dominant temporal frequency is the rate at which the intensity of the pseudocolor in the patterned region changes over time. Such a temporal regularity may e.g. cause blinking of a digital pseudocolor pattern at a certain frequency. An example of a dominant spatial frequency or, equivalently, rate of change is for example the width of a hatching or the spatial distance between a recurring geometric designs. Temporal and spatial variation may be combined, e.g. by having a temporally and spatially varying pattern, such as a blinking and/or moving hatching. The pseudocolor intensity at the location in the patterned region may change periodically with a frequency that depends on the intensity or brightness at the corresponding location in the input area. The change over time of the pseudocolor intensity may be continuous, e.g. sinusoidal, or abrupt, e.g. step-wise. The amplitude of the temporal change and/or the maximum or minimum intensity or brightness, may also depend on the intensity or brightness at the corresponding location in the input area.

According to another embodiment, a first pattern characteristic of the digital pseudocolor pattern of a location in the patterned region may be determined depending on the intensity or brightness at the matching location in the input area and second, different pattern characteristic of the digital pseudocolor pattern in the patterned region may depend on the average intensity or brightness in the input region. In more general terms, a first pattern characteristic at a location of the pseudocolor pattern in the patterned region may depend on a local characteristic at the matching location in the input area and a second, different pattern characteristic of the pseudocolor pattern in the patterned region may depend on a global characteristic of the input area. The global characteristic may be based on an image area which is larger than the area of a local characteristic. For example, the local characteristic may be determined using only a single pixel whereas the global characteristic may be determined using a plurality of pixels, where the plurality of pixels may include the single pixel for the local characteristic.

For example, the first pattern characteristic may be at least one of an intensity or brightness, and a contrast of the pseudocolor of the digital pseudocolor pattern and the second pattern characteristic may be at least one of a spatial and temporal rate of change of the digital pseudocolor pattern, such as a size of the pattern and a blinking frequency.

A digital input image may comprise one or more color channels. A single color channel may constitute a digital input image.

Alternatively or cumulatively, a position of a spatially varying pseudocolor pattern may be periodically shifted in subsequent digital output images. A geometry or topology of the spatially varying pattern may remain constant over time, e.g. in the subsequent digital output images, the geometry or topology comprising e.g. the width, distance and/or shape of the digital pseudocolor pattern. Such a temporally and spatially varying pattern may be perceived as moving in one direction by an observer.

According to another embodiment, a time series of digital output images may be computed or derived from a single digital output image. For example, a temporally varying pattern may be computed and displayed for one or more still input images. Alternatively, a temporally varying pattern is computed for each image in a time series of digital input images based on one or more subsequent digital input images.

It is preferred that the image processor is configured to compute the at least one digital output image comprising the digital pseudocolor pattern in real time. This allows an observer to react quickly and in time for critical changes in the digital input images, in particular if the digital input images represent a live stream of digital input images. In one embodiment, a single digital output image may be computed for each digital input image. In this embodiment, the frame rate of the digital output images may correspond to the frame rate of the digital input images.

The digital pseudocolor pattern may, in another embodiment, contain recurring geometric elements, e.g. polygons, stripes and/or circles. The digital pseudocolor pattern may, according to an alternative or cumulative embodiment, comprise pseudocolored areas and non-pseudocolored areas, and/or it may comprise pseudocolored areas and areas that do contain a different pseudocolor, or areas that contain a different intensity or brightness of the pseudocolor. For example, an ambiguous region of interest, which may qualify for two different kind of regions of interest may be marked in two different pseudocolors that are assigned to the two different kinds respectively. For example, if, in the input area, the fluorescence of two fluorophores overlaps and each of the two fluorophores is assigned a different pseudocolor, the pseudocolor pattern in the patterned region may contain the two pseudocolors of the two fluorophores, e.g. in a two-colored hatching. The same may hold for venous and arterial blood vessels: in a case where a venous blood vessel may not be distinguished with certainty from an arterial blood vessel, a two-colored, e.g. red and blue, digital pseudocolor pattern may be used.

In a more generalized sense, the pseudocolor pattern in the patterned region may comprise at least one of a first pattern component and a second pattern component, the first pattern component having one of a form, pseudocolor, pseudocolor intensity and a pseudocolor brightness being different from that of the second pattern component. For example, the second pattern component may have a lower pseudocolor intensity or brightness and/or different pseudocolor than the first pattern component.

For example, the first pattern component may be the part of a hatched pseudocolor pattern that comprises a pseudocolored region, whereas the second pattern component comprises the areas between the hatched lines and consequently has less or no pseudocolor intensity or brightness. The difference between the pseudocolor intensity or brightness of the first pattern component and the second component, or the contrast between the first and the second pattern component, may depend on one of an intensity and brightness in the input area of one or more digital input images. Thus, the contrast, i.e. the visibility of the pseudocolor pattern depends on the intensity or brightness of the input area. The contrast of the digital pseudocolor pattern may increase with the intensity or brightness in the input area.

In such an embodiment, an input area which has only low intensity or brightness and thus would hardly be visible or discernible, would contain a pattern having low contrast. Although the visibility of the pattern is increased as compared to the unpatterned input area due to the spatial and/or temporal frequencies in the pattern, it is not overly exaggerated. Thus, in this embodiment, the risk is further reduced that a pseudocolor pattern based on an input area having weak intensity or brightness is confused with an input pattern based on an input area having high intensity or brightness.

In another embodiment, the image processor may be configured to set one of the brightness and intensity of the at least one pseudocolor at a location in the patterned region proportional to one of the brightness and intensity at a corresponding location in the input area. Thus, the contrast of the pseudocolor pattern depends on the brightness and intensity of the corresponding location in the input area. This allows an observer to make immediate conclusions about the input area and thus about any ambiguity of the patterned region as a location of interest. For example, with decreasing brightness and intensity, the brightness and intensity of the at least one pseudocolor may decrease.

If the pseudocolor pattern comprises both a first and second pattern component, it may be preferred that the second pattern component does not comprise any pseudocolor. Thus, in this embodiment, the lower the intensity or brightness of the corresponding location in the input area is, the less visible the pseudocolor pattern in the patterned region will become automatically.

In one embodiment, the image processing device may be configured to compute a pseudocolored region in the one or more digital output images in addition to the patterned region. The pseudocolored region may be colored in a pseudocolor without use of a digital pseudocolor pattern. More specifically, the pseudocolored area may be computed using the device and method of EP 3 205 254, which is herewith incorporated in its entirety by reference. The pseudocolored region in the one or more digital output images may be at a location, in which the intensity or brightness of the corresponding input area in the one or more digital input images is above a predetermined lower threshold.

The device and method of EP 3 205 254 may also be used to merge the pseudocolor pattern with one or more digital input images.

If, for example, a fluorophore is used which binds to tumorous cells, a high fluorescence intensity or brightness may be generated in an area where many tumorous cells are concentrated. Thus, above a certain predetermined threshold of fluorescence intensity or brightness, there is a high certainty that high fluorescence intensity marks a tumor. Below this upper threshold, there may be an increased statistical uncertainty whether there is a tumor. In this embodiment, the input area having intensities or brightnesses above the threshold will be uniformly colored using a pseudocolor without a pattern. This may be done e.g. by merging the pseudocolor with one of the one or more digital input images by setting the intensity or brightness of the pseudocolor depending on the intensity or brightness in another one of the one or more digital input images, as described in EP 3 205 254. The input area having intensities or brightnesses below the threshold may be used to generate the patterned area as described above. The patterned area thus marks ambiguous regions of interest.

In a further embodiment, it may be preferred to determine the input area, or the patterned area respectively, by comprising one or more preferably contiguous pixels, of which the intensity or brightness is both below the upper predetermined threshold and above a lower predetermined threshold. The lower predetermined threshold may be used to avoid the inclusion of small intensities or brightness in the input area, which may be affected by noise or measurement errors.

A digital input image may comprise a plurality of separate input areas if the threshold criteria is met at different locations.

The one or more digital input images may comprise a fluorescence image which has been recorded in a fluorescence spectrum of at least one fluorophore; a digital white-light image recorded in white light; a digital CT image; a digital MRT image; a digital Raman microspectroscopy image; a digital ultrasound image; and any combination thereof.

The image processor may be further configured to select as the input area an area of the digital input image only if it comprises a plurality of preferably contiguous pixels. For example, the input area may be selected to be larger than a predetermined geometric shape of the digital pseudocolor pattern.

In one embodiment, the image processor may be configured to select as the input area, an area of the digital input area only if it comprises a predetermined minimum number of pixels in which an intensity or brightness is at least one of below and above a respective upper and lower threshold. For example, the minimum size of an input area may be 3×3, 4×4, or 5×5 pixels.

The image processor may be further configured to apply a different minimum size criterion or filter of the input area depending on an average intensity or brightness of the one or more digital input images in the input area and/or depending on the contrast between the input area and its immediately surrounding area. In this embodiment, it is considered that small, bright areas may be as visible and as relevant for a region of interest as a larger, less bright area. The size of the input area may thus depend on its average intensity or brightness. The larger the average intensity, the smaller the size of the input may be.

The average intensity or brightness may be any one of a median; an arithmetic, geometric, harmonic, quadratic, cubic, generalized, weighted, truncated, winsorized and interquartile mean; a mode; a midrange; and any combination of these values.

The image processor may, in another embodiment, be configured to compute an average intensity in the input area and in an area surrounding the input area, and, in particular, the contrast between the input area and its surroundings. The image processor may be configured to adjust a threshold to the minimum size of the input area depending on this difference. Using this criterion, it is considered that an input area which has an intensity or brightness that is markedly different from its surroundings, may qualify with a higher likelihood as a true region of interest.

The surrounding area may be located in the same or a different digital input image as the digital input image in which the input area is located. For example, the intensity or brightness of the input area may be computed from a digital fluorescence image.

The intensity or brightness of the surroundings may be determined from a digital white-light image. Alternatively, the intensity or brightness in the input area may be determined from a single color channel whereas the intensity or brightness of the surroundings is determined from another color channel or a combination of color channels.

The upper and/or lower threshold which is used to determine the input area and thus a region of interest, may be computed by the image processing device as depending on the average intensity or brightness of the input area, on a contrast between an average intensity or brightness of the input area and/or a surrounding area in the same or different digital input image. For example, the upper threshold may be increased in an input area, which has a high average intensity or brightness as compared to an input area which has a lower average intensity or brightness. The upper threshold may alternatively or additionally be increased in an input area, which has a high contrast to the surrounding area in the same or different digital input image as compared to an input area which has a lower contrast to those surroundings. The upper and/or lower threshold may also be determined by the image processing device depending on an overall average intensity or brightness in the digital input image where the input area is located, or another digital input image. For example, the upper and/or lower threshold may be increased if the overall intensity of the digital input image, in which the input area is located, is larger. Conversely, the upper and/or lower threshold may be decreased if the overall intensity of the digital input image, in which the input area is located, is smaller.

The image processing device may, in another embodiment, comprise a table or function for determining at least one of a value of an upper and/or lower threshold, and a size of the input area depending on at least one of an average intensity in the input area, in the surrounding area of the same or a different digital input image, and the difference or contrast between the intensity and the input area and the surrounding area in the same or a different digital input image. These values and sizes may be determined experimentally and stored in a memory device. Further, a neural network may be determined to teach in these values and sizes during operation of the image processing device.

In another embodiment, the image processor may be configured to vary a pattern characteristic depending on the size of the input area. For example, the image processor may be configured to adapt the geometric shape of the digital pseudocolor pattern to the size of the input area, such that more than one instance of the pseudocolor pattern fits into the input area. In another example, the image processing device may be configured to select the pseudocolor pattern dependent on the input area having the smallest size. In another additional or cumulative embodiment, the image processor may be adapted to automatically select between a temporally and a spatially varying patterning depending on the minimum or average size of the input area. For example, if the input area is small, a blinking pseudocolor with no spatial regularity may be used.

In another embodiment, the image processing device may be configured to apply the pseudocolor pattern in the patterned region only if the patterned region comprises at least a predetermined number of pixels. The image processor may be configured to determine at least one of the number of pixels, a dimension such as the width and/or length, and an aspect ratio of the input area and/or the patterned region. The image processor may be configured to compare this value with a predetermined value to determine whether the patterned region has at least one of a minimum number of pixels, dimensions, and aspect ratio.

The patterned region or the input area may comprise an area which would otherwise not be patterned, if this area is surrounded by the input area and does not exceed a predetermined size. If, for example, an otherwise bright input area comprises a dark speck, it may be preferred for easier recognition to also pattern this dark speck if it is only small.

In another advantageous embodiment, the image processor may further be configured to adjust the pattern characteristic at a location at a border of the patterned region depending on one of the intensity and brightness at least one neighboring location outside the patterned region of the at least one digital output image. For example, the intensity and brightness of the pseudocolor may be varied by the image processing device depending on the intensity or brightness at the least one neighboring location. This allows to smoothly adapt the intensity or brightness of the patterned region to the surroundings of the input area. The at least one neighboring location outside the patterned region must not necessarily be located in the same digital input image as the input area, but may be located in a different digital input image. This prevents the intensity or brightness from abruptly changing at the border of the patterned region, where in fact, the intensity or brightness of the input area tapers smoothly. Thus, the border is not artificially highlighted.

In another embodiment, the image processor may be configured to create a predetermined difference, or contrast, between one of the intensity and brightness of the at least one pseudocolor at a location at the border of the patterned region and at least one neighboring location outside the patterned region. This allows to maintain a specific contrast and thus visibility between the patterned region and its surroundings.

The image processor may be further configured to retrieve one of the one or more digital input images as a digital white-light image representing an object recorded in white light, and another one of the one or more digital input images as a digital fluorescence image representing the object recorded in the fluorescence spectrum of at least one fluorophore; to determine the input area in the digital fluorescence image; to merge the pseudocolor pattern with the digital white-light image, varying one of the brightness and intensity of the pseudocolor pattern at a location in the patterned region depending on one of the brightness and intensity of the corresponding location in the digital fluorescence image. Again, the merging may be performed using the device and method described in EP 3 205 254, as described above.

The image processor may be further configured to create a continuous transition in one of the brightness and intensity between a location at a border of the patterned region and neighboring location at the border outside of the patterned region.

In the medical observation device, the camera system may be configured to record at least one of the one or more digital input images in a fluorescence spectrum of at least one fluorophore as a digital fluorescence input image, and record one of the one or more digital input images in white light as a digital white light input image.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

In the following, exemplary embodiments are described with reference to the drawings. The specific combination of features shown in any drawing is for explanation only. Any of the features described above which is not contained in a specific feature, may be added to the embodiment shown in the figures. Conversely, any of the optional features described above may be omitted from the embodiment shown in a specific figure.

BRIEF DESCRIPTION OF THE DRAWING VIEWS

In the drawings:

FIG. 1 shows a schematic representation of a possible embodiment of a medical observation;

FIGS. 2-6 show schematic representation of digital pseudocolor patterns;

FIG. 8 shows a schematic representation of an input area;

FIG. 9 shows a schematic representation of another embodiment of an input area;

FIG. 10 shows a schematic representation of a pseudocolor intensity and/or brightness variation along a line in a patterned region;

FIG. 11 shows a schematic representation of another embodiment of a pseudocolor intensity and/or brightness variation along a line in a patterned region;

FIG. 14 shows a schematic representation of a flowchart.

DETAILED DESCRIPTION

Figure 7:
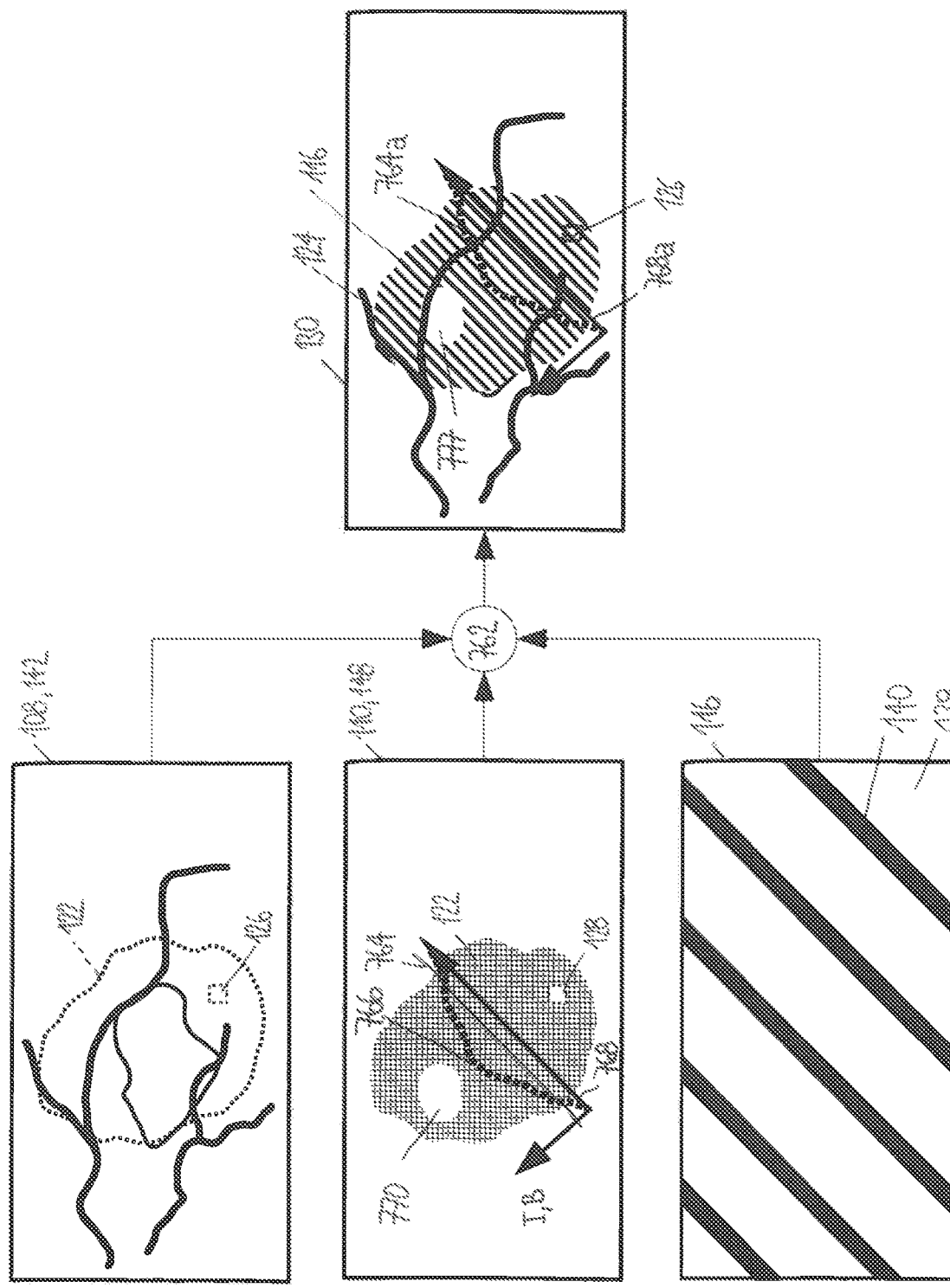
FIG. 7 shows a schematic representation of merging digital input images and a digital pseudocolor pattern to obtain an output image.

In FIG. 1, an image processing device 100 as e.g. used in a medical observation device 102, such as microscope 104 or endoscope is shown. The image processing device 100 comprises an image processor 106 which may be part of a general-purpose computer. The image processor 106 may comprise hardware, software or a combination of hardware and software. It may comprise a CPU, GPU, vector processor, FPA, and/or an ASIC.

The image processor 106 is configured to obtain a digital pseudocolor pattern 116. The digital pseudocolor pattern 116 has a pattern characteristic 118 and comprises a regularly varying pseudocolor 120.

The image processor 106 is further configured to combine the digital pseudocolor pattern 116 with an input area 122 of a retrieved digital input image 108, 110. A digital input image may comprise one or more color channels. A single color channel may already constitute a digital input image.

The combination of the digital pseudocolor pattern 116 with the input area 122 and/or a matching area of one of the digital input images 108, 110, results in a patterned region 124. The image processor 106 is also configured to vary the pattern characteristic 118 at a location 126 in the patterned region 124 depending on one of the intensity and brightness at a corresponding location 128 in the input area 122 of at least one of the digital input images and a further retrieved digital input image. The pattern characteristic 118 may comprise at least one of the pseudocolor, intensity, brightness, transparency, contrast, geometric shape, temporal rate of change and spatial rate of change of the digital pseudocolor pattern 116. The pattern characteristic 118 may, in particular, be an optical or visual characteristic, so that the various digital pseudocolor patterns 116 can be discerned visually from one another.

Different pattern characteristics 118 allow to distinguish different pseudocolor patterns 116 from another which may be used simultaneously in one digital output image 130. Any one pattern characteristic or any combination of these pattern characteristics 118 may be varied at the location 126 depending on one of the intensity and brightness at the corresponding location 128 in the input area 122.

The image processor 106 is further configured to output at least one digital output image 130 comprising the patterned region 124.

The image processor 106 may be configured to generate the patterned region 124 in an input area 122, in which one of an intensity or brightness in the one or more digital input images 108, 110 is at least one of below and above a respective upper and lower threshold. The intensity or brightness in the input area 122 may be computed by the image processing device 100 using an average intensity over the input area 122. The average intensity may be computed using at least one of a median; an arithmetic, geometric, harmonic, quadratic, cubic, generalized, weighted, truncated, winsorized and interquartile mean, a mode, a midrange and any combination thereof.

The input area 122 preferably comprises a plurality of pixels 128c. The pixels 128c of the plurality are preferably contiguous, i.e. form a connected area. The area may enclose one or more pixels 128c, which are not part of the input area 122, because their intensity or brightness does not meet the criterion for being an input area. This may for example be the case, if the intensity or brightness is below a lower predetermined threshold or if the intensity or brightness is above an upper predetermined threshold.

The image processor 106 may be further configured to adjust the pattern characteristic 118 at a location 132 at the border 134 of the patterned region 124 depending on one of the intensity or brightness and at least one neighbouring location 136 outside the patterned region 124 of the at least one digital output image 130.

The location 128, at which one of the intensity and brightness in the input area 122 is determined, may be a single pixel 128c. Correspondingly, the matching location 126 in the patterned region 124 may also be a single pixel 126c. In another embodiment, the location 128 may comprise a set of preferably contiguous pixels 126c in one or more digital input images 108, 110. In this case, the average intensity or brightness across the plurality of pixels may be determined. If more than one digital input image 108, 110 is used to determine the intensity or brightness, matching locations 126 are used. In another embodiment, the location 128 may comprise the entire input area 122.

A location 128 in the input area 122 corresponds to or, equivalently, matches a location 126 in the patterned region 124 if it has the same geometrical position within the at least one digital input image 108, 110 as in the at least digital output image 130. Alternatively, two locations 126, 128 may be considered to match, if they have the same geometrical position within the same image feature as extracted by a pattern recognition algorithm from the one or more digital input images 108, 110.

The input area 122 may be a feature 154 that has been extracted by the image processor 106 using a pattern recognition algorithm. An example of such a feature 154 is a blood vessel in a digital white-light image 142, which has been recorded in white light, or a tumor which has been recorded in the fluorescence spectrum of the fluorophore 150 in a digital fluorescence image 148.

In another embodiment, the image processor 106 may further be configured to create a predetermined difference between the intensity or brightness of the at least one pseudocolor 120 at a location 132 at the border 134 of the patterned region 124 and one of the intensity and brightness of at least one neighbouring location 136 outside the patterned region 124.

In another embodiment, the image processor 106 may be further configured to set one of the brightness and intensity of the at least one pseudocolor 120 at a location 126 in the patterned region 124 proportional to one of the brightness and intensity at a corresponding location 128 in the input area 122.

The digital pseudocolor pattern 116 in the patterned region 124 may comprise a first pattern component 138 and a second pattern component 140. A pseudocolor brightness or intensity of the first pattern component 138 is preferably different from the pseudocolor brightness or intensity of the second pattern component 140. In another variant, the first pattern component 138 and the second pattern component 140 may comprise different pseudocolors.

The pseudocolor brightness or intensity in at least one of the first and second pattern components 138, 140 may depend on the brightness or intensity, respectively, in the input area 122. In particular, the difference between the pseudocolor intensity or brightness of the first component and that of the second pattern component at a location 126 may be dependent on the intensity and brightness at the matching location 128 in the input area 122. For this, the location 126 may have a size which comprises both pattern components 138, 140.

FIGS. 2 to 6 show examples of various digital pseudocolor patterns 116 indicated as 116a, 116b, 116c, 116d, 116e. The patterns 116a-116e all have spatial and/or temporal regularity. The patterns of FIGS. 2 and 6 should not be construed to limit the variety of pseudocolor patterns 116 that may be used by the image processing device 100 in any way.

Pseudocolor patterns 116a-116d all have spatial regularity. Thus, a basic constituent of the digital patterns 116a-116d repeats itself at a certain spatial frequency. The basic constituent may be of any shape, such as a polygonal shape as in pseudocolor pattern 116a of FIG. 2. The pseudocolor pattern 116 may be a hatching as the pseudocolor patterns 116b-116d.

As further shown in FIGS. 2 to 6, the pattern components 138, 140 of a pseudocolor pattern 116a-116e have different pseudocolor brightness or intensity. One of the two components 138, 140 in FIGS. 2 to 6 may have less intensity or brightness of the pseudocolor than the other. In FIGS. 2, 4, 6, the first pattern component 138 may not contain any pseudocolor, whereas the second pattern component 140 comprises a pseudocolor. In pattern 116b, the first pattern component 138 comprises a pseudocolor at a lower intensity than the second pattern component 140.

The pseudocolor patterns 116d-116e of FIGS. 5 and 6 have temporal regularity. In the pseudocolor pattern 116d of FIG. 5, the shape of the pseudocolor pattern 116d, here a hatching as an example, does not change shape, but position over time t: By shifting the position gradually from one frame 556 to the next, the impression of a pseudocolor 116d propagating in a direction 558 may be created. By repeating a sequence of subsequent frames 556 at a certain temporal rate, or, equivalently, frequency, regularity over time t is obtained. Thus, the digital pseudocolor pattern 116d of FIG. 5 has both spatial and temporal regularity.

In FIG. 6, the digital pseudocolor pattern 116e exhibits temporal regularity only in that the first pattern component 138 and the second pattern component 140 are displayed at a certain temporal rate of change or frequency, respectively. This creates a blinking pseudocolor pattern 116e.

The image processor 106 may be configured to vary at least one of a temporal and spatial rate of change of the digital pseudocolor pattern 116 depending on one of an intensity and brightness in the input area 122. For example, a distance 460 between one of the first and second pattern component 138, 140, or a width thereof, may depend on the intensity or brightness in the input area 122. For example, the distance 460 between the second pattern component 140 having a higher pseudocolor intensity or brightness may increase if the intensity or brightness in the input area 122 increases.

The image processor 106 may be configured to retrieve at least one of the one or more digital input images 108, 110 as a digital white-light image 142. The digital white-light image 142 represents an object 144 recorded in white light 146. The white light 146 contains enough wavelengths to faithfully render any color of the object 144 in the visible light frequencies. For example, a digital white-light image 142 may be in RGB format.

The image processor 106 may further be configured to retrieve at least another one of the one or more digital input images 108, 110 as a digital fluorescence image 148. The digital fluorescence image represents the object 144 recorded in the fluorescence spectrum of at least one fluorophore 150. If the object contains a plurality of fluorophores, a plurality of digital fluorescence images 148 may be provided, each of the digital fluorescence images 148 preferably containing the fluorescence wavelength of a different fluorophore 150.

The image processing device 100 may further be configured to determine the input area 122 in the at least one digital fluorescence image 148. For example, the input area 122 may be determined to correspond to an area in a digital fluorescence image 148 in which the fluorescence brightness or intensity is above a lower threshold and below an upper threshold. Alternatively, the input area may be determined as an area in the digital fluorescence image 148, in which the intensity or brightness is above the lower threshold, or as an area in which the intensity or brightness is below the upper threshold. The digital fluorescence image 148 may be normalized and/or low-pass filtered, before determining the input area.

If more than one digital fluorescence image 148 is retrieved by the image processor 106, an input area 122 may be determined independently in each of the digital fluorescence images 148. For example, if one digital fluorescence image 148 records the fluorescence spectrum of a fluorophore 150 which binds to oxygen-rich red blood cells, determination of the input area 122 by using at least one brightness or intensity threshold may be used so that the input area 122 will correspond to an arterial blood vessel. If another fluorophore 150a (FIG. 1) is used to mark tumor cells, a digital fluorescence image 148 containing the fluorescence spectrum of this other fluorophore 150a may be used to define a tumor as an input area 122. Preferably, two different digital pseudocolor patterns are assigned to these two different input areas 122 which are based on different digital input images 108, 110, or digital fluorescence images 148 in particular. The two different digital pseudocolor patterns differ in at least one pattern characteristic 118, e.g. the pseudocolor.

The image processor 106 may further be configured to merge the pseudocolor pattern 116 with the digital white-light image 142, wherein the brightness or intensity of the pseudocolor pattern 116, e.g. of at least one of its components 138, 140 at a location 126 in the patterned region 124 is set depending on the brightness or intensity of the corresponding location 128a in the input area 122 of the digital fluorescence image 148.

The image processor 106 may be configured to retrieve the one or more digital input images 108, 110 from a camera system 112 or a memory device 114, each of which may be a part of the medical observation device 102. The one or more digital input images 108, 110 in the memory device 114 may have any appropriate data format for storing image information, such as PDF, GIF, TIF, JPEG, TGA, and/or MPG format. The memory device 114 may be a volatile or non-volatile memory. It may be a fixed part of the medical observation device 102 or it may be removable. The memory device 114 may for example be a hard disk, a memory bank, an optical disk, a memory card or a memory stick.

The camera system 112 is preferably configured to record one or more digital input images 108,110. For example, the camera system 112 may be configured to record at least one of the one or more digital white-light images 142 and the one or more digital fluorescence images 148. The camera system 112 may comprise at least one camera 112a. The camera system 112 may comprise an RGB camera for recording white-light images such as a CCD or CMOS camera. The camera system 112 may, in addition or alternatively, comprise a camera for recording UV, NIR and/or IR images. The camera system 112 may comprise a multi-spectral or hyperspectral camera. The medical observation device 102 may further comprise at least one display device 152 configured to display the at least one digital output image 130.

For example, the medical observation device 102 may comprise as a display device 152, a monitor 152a, the VR goggles 152b, and/or an ocular 152c. Any one of the display devices 152 may be stereoscopic or holographic. This allows to display digital input images 108, 110 which are 3-dimensional, such as stereoscopic digital input images 108, 110.

In FIG. 7, it is shown how a digital pseudocolor pattern 116 is combined or merged with a digital input image 108 representing e.g. a digital white-light image 142, and a digital input image 110, representing e.g. a digital fluorescence image 148. The digital white-light image 142 may be a color image or a monochrome image; the digital fluorescence image 148 may be a color image or a monochrome image. In the digital fluorescence image 148, an input area 122 has been determined by the image processing device 100 (FIG. 1). The combination of the digital pseudocolor pattern and the one or more digital input images 108, 110 results in at least one digital output image 130. The combination or merging function is exemplarily shown at reference numeral 762 and may employ the device and method described in EP 3 205 254 by using the digital pseudocolor pattern instead of a (constant) pseudocolor.

The input area 122 may be determined as an area in the digital fluorescence image 148, in which the intensity I or brightness B is above a lower threshold 764. An intensity or brightness variation 766 of the pseudocolor along line 768 is shown schematically for explanatory purposes. The input area 122 is also indicated in the other digital input image 108, the digital white-light image 142.

Before merging the two digital input images 108, 110, locations 126 and 128 are matched. This can, e.g. be accomplished by making sure that the field of views and preferably of the respective sensors which record digital input images 108, 110 are identical. In this case, the locations 126 and 128 match if they are within the same geometrical position in their respective digital input image 108, 110. In the merging 762, the digital pseudocolor pattern 116 is generated only for locations 128 in the input area 122. An area 770, which may be enclosed by or located outside input area 122 and which does not have an intensity or brightness above the lowest lower threshold 764, preferably is not assigned a pseudocolor pattern 116 in the one or more digital output images. The area 770 may therefore be considered as background.

At least one pattern characteristic 118 of the digital pseudocolor pattern 116 is varied by the image processing device 100 depending on the intensity or brightness at a location 128 in the digital fluorescence image 148 in the input area 122. For example, the intensity of at least one of the first and second components 138, 140 at the location 126 in the at least one digital output image 130 may depend on the brightness or intensity at the location 128. The intensity or brightness of the pseudocolor of at least one of the pattern components 140, 138 may be larger at a location 126 in the at least one digital output image 130, if the intensity or brightness at the matching location 128 in the digital fluorescence image 148 is larger than at another location. Alternatively, the contrast between the pattern components 138, 140 may be varied depending on the intensity or brightness at the location 128. For example, a location 128 having a larger intensity or brightness may result in the pseudocolor pattern 116 in the patterned region 124 to have higher contrast than at a location in the input area 122 of the digital fluorescence image 148 having lower intensity or brightness. Thus, the visibility of the patterned region 124 may increase with increasing intensity or brightness at the matching location 128 in the digital fluorescence image. Alternatively or cumulatively, a temporal and/or spatial rate of change at the location 128 may depend on the intensity or brightness of the matching location 126.

Line 768a of the at least one digital output image 130 matches line 768 in the digital fluorescence image 148. Along the line 768a, a variation 766a of the intensity or brightness of the pseudocolor of at least one pattern component 138, 140 of the patterned region 124 mirrors the intensity distribution 766 in the digital fluorescence input image 148.

Instead of the digital fluorescence image 148, another digital white-light color image or one or more color channels as a white-light image 142 may be used in a variant of FIG. 7. For example, the digital input image 110 in FIG. 7 may be the red channel of the RGB digital input image 108. In such a case, the intensity or brightness of the red color channel may e.g. be used to identify arterial blood vessels. Instead of or in addition to the digital white-light image 142, another digital fluorescence image 148 recorded in the fluorescence spectrum of a different fluorophore 150a (FIG. 1) may be used. In this additional fluorescence image, input areas may be determined for combination with a digital pseudocolor pattern having a different pseudocolor than the pseudocolor pattern used in the digital fluorescence image 148 of the fluorophore 150 so that the fluorophores can be distinguished visually.

In FIG. 8, an input area 122 of a digital input image 108, 110 is shown schematically. The input area 122 is defined by all those locations 128, in which the intensity I or brightness B is above a lower threshold 764 and, here, also below an upper threshold 872. Another input area 122a may be determined by the locations 128, in which the intensity I or brightness B is above the upper threshold 872.

The two different input areas 122, 122a are preferably assigned different digital pseudocolor patterns 116. The input area 122 is assigned a digital pseudocolor pattern 116 which differs in at least one pattern characteristic 118 from the digital pseudocolor pattern 116, which is assigned in the at least one digital output image 130, to the input area 122a. In a variant, the input area 122a may be assigned a uniform pseudocolor, preferably the same pseudocolor as the digital pseudocolor pattern 116 used in the patterned region 124 based on the input area 122.

Again, the input area 122 may contain one or more areas 770 which contains or consists of locations having intensity I or brightness B below the lower or lowest lower threshold 764.

The basic concept shown in FIG. 8 may be expanded to more than two input areas 122 in a digital input image 108, 110. For each region, there may be a respective lower threshold 764 and a respective upper threshold 872. This is schematically shown in FIG. 9, where an additional, third input area 122b has been determined by using a second pair of thresholds 764, 872.

The input areas 122, 122a, 122b are preferably assigned different digital pseudocolor patterns 116. In particular, the input area 122 having lower thresholds 764, 872 may be assigned a pseudocolor pattern having a lower contrast and/or a lower pseudocolor intensity or brightness, and/or a lower spatial and/or temporal rate of change than the digital pseudocolor pattern 116 assigned to an input area 122b having higher thresholds 764, 872.

In FIGS. 8 and 9, the different digital pseudocolor patterns 116 which are assigned to the respective input areas 122, 122a, 122b, represent different confidence levels of an input area 122 corresponding to a region of interest. A lower confidence level leads to a decreased visibility of the pseudocolor pattern in the respective area by varying at least one of the pattern characteristics.

For example, the input area 122a in FIGS. 8, 9 having intensities and brightnesses above the highest upper threshold 872, may represent an area which may, with a very high likelihood, represent a tumor. The input area 122a may therefore be marked in the at least one digital output image 130 with a uniform pseudocolor, whereas, with decreasing thresholds, the input areas 122, 122b are assigned increasingly less visible pseudocolor patterns to mark them as less probable outlines of a tumor.

In FIGS. 10 and 11, the patterned regions 124, 124a are shown that may e.g. result from two input areas 122, 122a as shown in FIG. 8. In FIG. 10, the intensity I or brightness B of the pseudocolor varies continuously across the border 134 between the pseudocolor patterns 116 of two neighbouring patterned regions 124, 124a. There will not be a jump in the intensity or brightness of the two adjacent patterned regions 124 across the border 134, at least in one of the pattern components 138, 140.

In FIG. 11, a predetermined jump 1176 in the intensity or brightness of the pseudocolor is generated automatically across the border 134. The smooth transition will avoid that undue attention is given to the transitions between neighbouring input areas 122 instead of the input area 122 itself. Thus, if for example the medical observation device 102 is a surgical microscope or endoscope, the surgeon's attention is not distracted towards the border 134. Introducing a predetermined jump 1176 at the border 134 will allow to put a predetermined emphasis to the border.

In FIG. 10, a schematic pseudocolor intensity distribution 1074 along a line 1076, crossing a patterned region 124 and an adjacent patterned region 124a, is shown. The patterned region 124a may, but need not, be located within the patterned region 124. In the example, the patterned region 124 comprises, just by way of example, a pseudocolor pattern 116 which is formed as a hatching.

Line 1076 follows the pattern component 140 of the hatching having the higher intensity or brightness of the pseudocolor of the two pattern components 138, 140. If a digital pseudocolor pattern 116 other than a hatching is used, such as polygons or circles, the same considerations apply. The only difference is that the intensity or brightness distribution 1074 would, in FIG. 10, exhibit the jumps in intensity or brightness between the two components 138, 140, i.e. the contrast of the digital pseudocolor pattern 116, along line 1076. The same applies if the patterned region 124 comprises a pseudocolor pattern, which has only temporal regularity, because it e.g. contains a uniformly distributed pseudocolor.

As can be seen in FIG. 10, the location 132 in the patterned region 124, which is located adjacent the border 134, has an intensity or brightness which forms a smooth and continuous transition to the intensity or brightness at the neighboring location 136 across the border 134, in the patterned region 124a. Here, the patterned region 124a may have a uniform pseudocolor. A smooth and continuous transition may be formed by e.g. establishing a smooth change of the intensity or brightness gradients across the border 134 or by assigning the same intensity or brightness at the locations 132, 136 on both sides of the border 134.

In FIG. 10, a second intensity or brightness distribution 1074a of the digital pseudocolor pattern is shown as an alternative to the intensity or brightness distribution 1074. In the intensity or brightness distribution 1074a, an additional factor such as distance to the border or a factor proportional to the intensity or brightness at the location 128 in the input area 122 may be used to amplify the fall-off in intensity in the patterned region 124 towards the background 770. In another variant, the intensity or brightness distribution 1074 is computed to have a smooth transition across the border 134 to adjacent region 124 and to fall off to a predetermined value at the border 134 to the background 770.

According to another example, the intensity of the pattern component 138 in the patterned region 124 may be computed by using the square of an intensity or brightness at location 128, which has been normalized to a maximum value of 1. The square intensity or brightness will exaggerate any fall-off in intensity or brightness.

FIG. 11 shows a variant where, at the border 134, a predetermined jump 1176 in the pseudocolor intensity or brightness between two neighboring locations 132, 136 across the border 134 is introduced by the image processing device 100. Introducing such a jump 1176 in the intensity or brightness across the border 134 makes the border more visible than the smooth transition shown in FIG. 10. The image processing device 100 may be configured to allow a user to set the predetermined jump 1176 e.g. by interaction with the image processing device 100, for example via a graphical user interface.

The image processing device 100 may be configured to identify an input area 122 only if it has a minimum size. The minimum size may comprise any one of a minimum number of pixels 128c which needs to be contained in an input area 122, a minimum area, a minimum aspect ratio of the input area, and any combination thereof. The minimum size does not need to be constant, but may be adaptive. This is shown with reference to FIG. 12.

The image processing device 100 may be configured to determine the minimum size depending on at least one of an average intensity or brightness in the input area 122, a difference, e.g. a contrast, between the average intensity or brightness of the input area 122 and at least part of the background 770, and an average intensity or brightness in the input area 122.

For determining the contrast of an input area, it is not necessary to compute the average intensity and brightness of the entire background 770 or the entire remainder of the digital input image 108, 110, in which the input area 122 is contained. In order to speed up the computational processes carried out by the image processing device 100, it may be sufficient to compute the contrast between the average intensity or brightness in the input area 122 and the average input intensity or brightness in an immediate surrounding 1278 of the input area 122. The immediate surroundings 1278 may e.g. have a predetermined depth, i.e. extend a predetermined number of pixels away from the input area 122, such as three to ten pixels. Alternatively or cumulatively, the immediate surroundings 1278 may be computed to contain the same number of pixels as the input area 122. If the input area 122 borders on one or more other input areas 122b, 122a, the immediate surroundings 1278 may comprise pixels of these input areas 122b, 122a.

Moreover, at least one of the lower thresholds 764 and upper threshold 872 may depend on either the absolute average intensity or brightness in the input area 122, the contrast between the average intensity or brightness of the input area 122 and either the remaining digital input image 108, 110, or the immediate surroundings 1278 of the respective input area 122. For example, at least one of the upper and lower thresholds 764, 872 may be automatically determined such that the contrast determined from the average intensity or brightness in the input area 122 and the average intensity or brightness of its immediate surroundings 1278 is constant.

Figure 12:
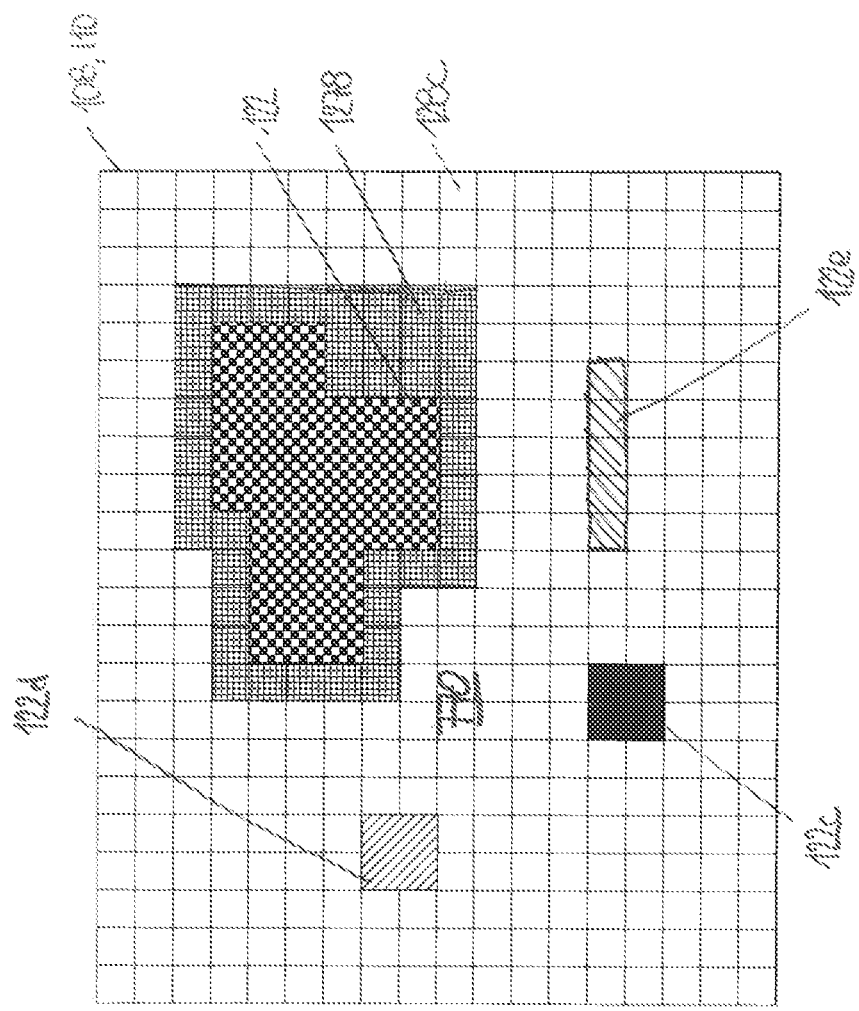
FIG. 12 shows a schematic representation of input areas in a digital input image.

As shown in FIG. 12, an input area 122c, which has very high absolute intensity or brightness, may be assigned a lower minimum size by the image processing device 100 than an input area 122d having a smaller absolute average intensity or brightness. The same may hold if the contrast between the respective input area 122c, 122d and the remainder of the digital input image 108, 110 or the immediate surroundings 1278 is considered. An input area 122d may be discarded although it has the same size as an input area 122c if its absolute average intensity or brightness and/or its contrast to its surroundings or to the remainder of the digital input image 108, 110, are below a threshold. An input area 122e may further be discarded if its aspect ratio is not within a predetermined range, e.g. because it is too elongated.

Figure 13:
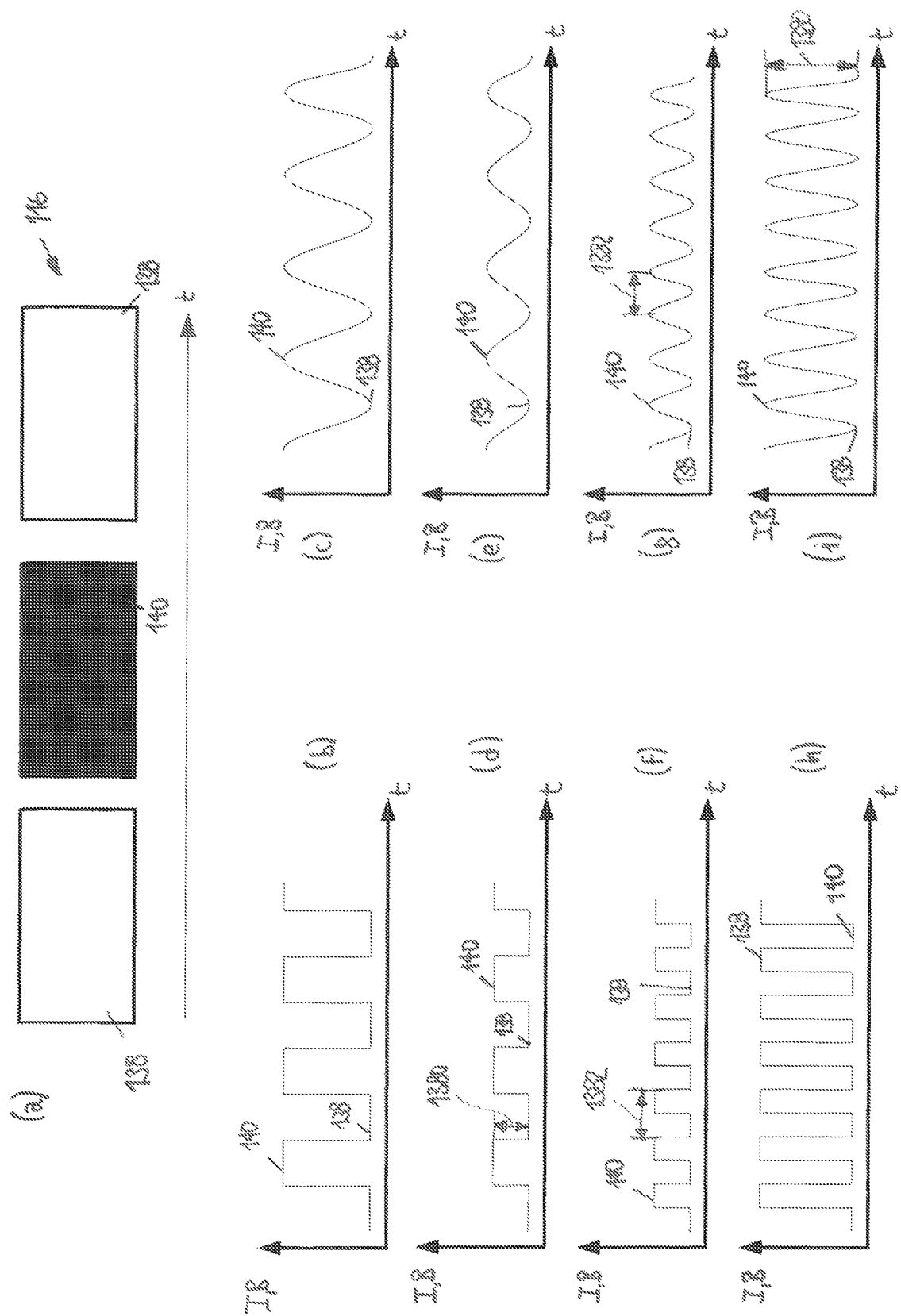
FIG. 13 shows a schematic representation of variants of a digital pseudocolor pattern.

In FIG. 13, it is shown how a pattern characteristic of a temporarily varying pseudocolor pattern 116 may be modified depending on the intensity or brightness of a location of an input area 122, such as e.g. shown in FIGS. 8 and 9.

In the example shown in FIG. 13, the temporal regularity is achieved by alternatingly and periodically displaying the first pattern component 138 and the second pattern component 140 over time as depicted in (a). The transition between the two pattern components 138 and 140, i.e. the transition between the intensity or brightness of the pseudocolor in the pattern components 138, 140 may be stepwise as shown in (b), (d), (f) and (h), or smooth, for example, saw-tooth like, sinusoidal, as shown in (c), (e), (g) and (i). Depending on the intensity and brightness at a location 128, at least one of the amplitude 1380 or, equivalently, the contrast between the pattern components 138 and 140, or the frequency 1382 may be changed.

In another embodiment, one pattern characteristic may depend on the average intensity and brightness in the input area 122, whereas another pattern characteristic may depend on the intensity or brightness at a location 126 within the input area 122. For example, the temporal rate of change, period or the frequency 1382 of the digital pseudocolor pattern 116 may depend on the average intensity and brightness of the input area 122. Thus, the entire input area 122 will have a uniform blinking rate. The amplitude 1380 at a location 128 in the patterned region 124 may depend on the intensity or brightness at the matching location 126 in the input area 122.

The same may of course also be applied to a spatially varying digital pseudocolor pattern 116 if, for example, the temporal rate of change is replaced by the spatial rate of change and the amplitude by local contrast or local intensity or brightness. In such a case, the geometry (spatial rate of change) of the digital pseudocolor pattern 116 may depend on the average intensity or brightness in the input area 122, whereas the local contrast may depend on the intensity or brightness of the location 126 in the input area 122.

FIG. 14 shows a schematic representation of a flow chart of the method described above.

In a first step 1484, a digital input image 108, 110 is obtained. For example, in step 1484, a digital fluorescence input image 148 recorded in the fluorescence spectrum of a first fluorophore 150 may be obtained. In a second optional step 1484a, a second digital fluorescence input image 148 recorded in the fluorescence spectrum of a second fluorophore 150a may be obtained. Preferably, the fluorescence spectra of the two fluorophores 150, 150a are different. In a step 1484b, a digital white-light image 142 may be obtained. The step of obtaining a digital input image 108, 110 may comprise at least one of recording the digital input image 108, 110 with at least one camera 112 and retrieving the digital input image 108, 110 from the memory device 114. Steps 1484, 1484a and 1484b may be performed in parallel or sequentially.

In a step 1486, preprocessing of the digital input image 108, 110 may take place. The preprocessing 1486 may be different for each different type of digital input image. For example, preprocessing 1486 may comprise any type of normalizing, correcting optical distortions, unsharp masking, deconvolution and any type of filtering.

In a step 1490, one or more input areas 122 may be determined in the respective digital input image e.g. by applying at least one of an upper and a lower brightness and intensity threshold. This step may be carried out in one or more of the obtained digital input images 108, 110. There may be one or more digital input images 108, 110 in which no input area 122 is determined, e.g. in FIG. 14, the digital white-light image. However, in another embodiment, an input area 122 may also be determined in one or more digital white-light images.

In the next step 1492, a digital pseudocolor pattern is obtained and combined with at least one input area 122 in at least one of the one or more digital input images 108, 110 to create a patterned region 124. The digital pseudocolor pattern 116 may be retrieved from the memory device 114 or be generated using a function, which is stored in the memory device 114.

In step 1494, at least one pattern characteristic 118 at a location of the patterned region 124 is adjusted depending on one of an intensity and brightness at a corresponding location in the input area 122 of at least one of the one or more digital input images 108, 110.

It may be noted, that steps 1492 and 1494 may be carried out as a single step. For example, the adjustment may be part of the combining step.

At step 762, the digital input images and the digital pseudocolor pattern 116 are merged to generate at least one digital output image 130.

Again, step 762 may occur simultaneously with any one of steps 1492 and 1494. For example, the patterned region 124 may be generated in one step in the at least one digital output image 130 when obtaining and adjusting the digital pseudocolor pattern 116. In step 1496, the at least one digital output image is output for further processing or for displaying.

REFERENCE NUMERALS 100 image processing device
102 medical observation device
104 microscope
106 image processor
108 digital input image
110 digital input image
112 camera system
112a camera
114 memory device
116 digital pseudocolor pattern
116a-e digital pseudocolor patterns
118 pattern characteristic
120 pseudocolor
122 input area
122a-e various input areas
124 patterned region
124a patterned region
126 location in patterned region
126c pixel
128 matching location in input area
128c pixel
130 digital output image
132 location at the border of the input area
134 border of an input area
136 neighbouring location across the border
138 first pattern component
140 second pattern component
142 digital white-light image
144 object
146 white light
148 digital fluorescence image
150 fluorophore
150a further fluorophore
152 display device
152a monitor
152b VR goggles
152c ocular
154 image feature
460 distances
556 frame
558 propagation direction
762 merging function
764 lower threshold
766 intensity distribution
766a variation of intensity distribution
768 line
770 background
872 upper threshold
1074 intensity or brightness distribution
1074a intensity or brightness distribution
1076 line
1176 brightness or intensity jump across border
1278 surroundings of input area
1380 amplitude
1382 frequency
1484 obtaining a digital input image
1484a obtaining a digital input image
1484b obtaining a digital input image
1486 preprocessing
1490 determining input area
1492 obtaining a digital pseudocolor pattern
1494 adjusting pattern characteristic
1496 further processing and/or displaying
I intensity
B brightness
t time

What is claimed is:

1. An image processing device (100) for a medical observation device (102), wherein the image processing device comprises an image processor (106), the image processor being configured
to obtain a digital pseudocolor pattern (116), the digital pseudocolor pattern having a first pattern characteristic (118) and a second pattern characteristic (118) different from the first pattern characteristic, and the digital pseudocolor pattern comprising a pseudocolor (120);
to combine the digital pseudocolor pattern with an input area (122) of a retrieved digital input image (108, 110), thus forming a patterned region (124);
to vary the first pattern characteristic of the digital pseudocolor pattern at a location (126) in the patterned region depending on a local characteristic at a matching location (128) in the input area and vary the second pattern characteristic of the digital pseudocolor pattern in the patterned region depending on a global characteristic of the input area; and
to output at least one digital output image (130) comprising the patterned region.

2. The image processing device (100) according to claim 1, wherein the input area (122) is an area in which an intensity (I) or a brightness (B) in the obtained digital input image (108, 110) is at least one of below an upper threshold (872) and above a lower threshold (764), and the image processor (106) is configured to form the patterned region (124) in the input area (122).

3. The image processing device (100) according to claim 1, wherein the image processor (106) is configured to select as the input area (122) an area which has at least one of a minimum number of pixels (128c), a minimum difference between an average intensity or brightness of the input area (122) and at least part of the immediate surroundings (1278) of the input area (122), and a minimum average intensity (I) or brightness (B).

4. The image processing device (100) according to claim 1, wherein the image processor (106) is further configured to adjust another pattern characteristic (118) of the digital pseudocolor pattern at a location (132) at a border (134) of the patterned region (124) depending on one of the intensity (I) and brightness (B) of at least one neighboring location (136) outside the patterned region (124) of the at least one digital output image (130).

5. The image processing device (100) according to claim 1, wherein the image processor (106) is further configured to create a predetermined difference between one of the intensity (I) and brightness (B) of the pseudocolor (120) at a location (132) at a border (134) of the patterned region (124) and one of the intensity and brightness at least one neighboring location (136) outside the patterned region (124).

6. The image processing device (100) according to claim 1, wherein the image processor (106) is further configured to set one of the brightness (B) and intensity (I) of the at least one pseudocolor (120) at the location (126) in the patterned region (124) proportional to one of the brightness (B) and intensity (I) at the matching location (128) in the input area (122).

7. The image processing device (100) according to claim 1, wherein the pseudocolor pattern (116) in the patterned region (124) comprises a first pattern component (138) and a second pattern component (140), the first pattern component having one of a pseudocolor intensity and a pseudocolor brightness being different from that of the second pattern component, the difference being dependent on one of an intensity and a brightness in the input area (122).

8. The image processing device (100) according to claim 1, wherein the image processor (106) is configured to vary at least one of a temporal and a spatial rate of change of the digital pseudocolor pattern (116) depending on one of an intensity and brightness in the input area (122).

9. The image processing device (100) according to claim 1, wherein the image processor (106) is configured
- to retrieve the digital input image (108, 110) or another digital input image (108, 110) as a digital white-light image (142) representing an object (144) recorded in white-light (146), and another digital input image (108, 110) or the digital input image (108, 110) as a digital fluorescence image (148) representing the object (144) recorded in the fluorescence spectrum of at least one fluorophore (150);
- to determine the input area (122) in the digital fluorescence image; and
- to merge the pseudocolor pattern (116) with the digital white-light image (142), varying one of the brightness and intensity of the pseudocolor pattern at the location (126) in the patterned region (124) depending on one of the brightness and intensity of a corresponding location (128*a*) in the input area (122) of the digital fluorescence image.

10. A medical observation device (102) comprising:
the image processing device (100) according to claim 1;
a camera system (112) configured to record one or more digital input images (108, 110); and
at least one display device (152) configured to display the at least one digital output image (130).

11. The medical observation device (102) according to claim 10, wherein the camera system (112) is configured to record one of the one or more digital input images (108, 110) in a fluorescence spectrum of at least one fluorophore (150) as a digital fluorescence image (148) and/or record another of the one or more digital input images (108, 110) in white-light as a digital white-light input image (142).

12. The medical observation device (102) according to claim 10, wherein the medical observation device comprises a microscope (104) or an endoscope.

13. An image processing method comprising the following steps:
retrieving one or more digital input images (108, 110);
generating at least one digital output image (130) based on the one or more digital input images; and
outputting the at least one digital output image for at least one of displaying and further processing;
wherein the step of generating the at least one digital output image from the digital input image comprises the steps of:
combining a digital pseudocolor pattern (116) with at least one input area (122) of at least one of the one or more digital input images to create a patterned region (124), wherein the digital pseudocolor pattern has a first pattern characteristic (118), a second pattern characteristic (118) different from the first pattern characteristic, and a pseudocolor (120);
adjusting the first pattern characteristic (118) of the digital pseudocolor pattern at a location (126) in the patterned region depending on a local characteristic at a matching location (128) in the corresponding input area of at least one of the one or more digital input images; and
adjusting the second pattern characteristic (118) of the pseudocolor pattern (116) in the patterned region depending on a global characteristic of the corresponding input area.

14. The method according to claim 13, wherein a continuous transition is created in one of the brightness and intensity of a location (132) at a border 134 of the patterned region (124) and a neighboring location (136) outside of the patterned region (124).

15. A non-transitory computer readable storage medium comprising a program comprising instructions which, when the program is executed by a computer, cause the computer carry out the method according to claim 13.

* * * * *